US00PP10115P

United States Patent [19]

Jackson et al.

[11] Patent Number: Plant 10,115

[45] Date of Patent: Nov. 11, 1997

[54] APPLE TREE NAMED 'JACKSON'

[76] Inventors: William T. Jackson; Shirley W. Jackson, both of P.O. Box 1191, Bowling Green, Ky. 42102

[21] Appl. No.: 629,353

[22] Filed: Apr. 8, 1996

[51] Int. Cl.[6] ..... A01H 5/00

[52] U.S. Cl. ..... Plt./34.1

[58] Field of Search ..... Plt./34.1

[56] References Cited

U.S. PATENT DOCUMENTS

| | | | |
|---|---|---|---|
| P.P. 85 | 1/1934 | Uecker | Plt./34.1 |
| P.P. 2,650 | 7/1966 | Synder | Plt./34.1 |
| P.P. 2,934 | 10/1969 | Robison et al. | Plt./34.1 |
| P.P. 5,086 | 8/1983 | Carnefix | Plt./34.1 |
| P.P. 5,838 | 12/1986 | Akins | Plt./34.1 |
| P.P. 6,406 | 11/1988 | Higgins | Plt./34.1 |
| P.P. 8,701 | 4/1994 | Thome | Plt./34.1 |

*Primary Examiner*—James R. Feyrer

[57] ABSTRACT

A new and distinct variety of 'Jonathan' apple tree originating as a limb mutation of the *Malus sylvestris* variety of 'Jonnee', Robison cultivar (U.S. Plant Pat. No. 2,934)

This new sport is unique from its parent because the fruit starts coloring 30 days earlier and the color develops as a solid, rich red blush with no striping. The color finishes virtually 100% solid as a deep ruby red. Fan 1, Red Group 46A to 45C.

The commercial harvest maturity is 7 days earlier than its parent. At harvest, the internal flesh color is much creamier yellow color that the parent. Fan 1, Yellow Group 11 D. The fruit skin is significantly smoother and much less prone to stem end russet and scarf skin than its parent.

1 Drawing Sheet

BACKGROUND OF THE INVENTION

The subject of this disclosure is a new, earlier and earlier ripening tree within the 'Jonathan' apple market class. The variety 'Jonathan', an old, established and popular variety is known for its desirable characteristics. It has a round conic, regular shape which is rich in red color. The fruit of the original tree, while classified as a red apple, was characterized by containing numerous straw yellow spots on the skin surface, caused, in part, by shading by leaves and stems. The fruit has medium to long fruit stems, and a wide basin with abrupt shoulders. The attractive appearance, flavor and keeping quality of 'Jonathan' led to its popularity in apple markets, and initiated new plantings of the tree. By the late 1960's 'Jonathan' ranked within the top five most planted varieties within the United States, and plantings of this tree continued to increase. With increased plantings, color sports of 'Jonathan' were discovered and further expanded the market class and popularity of fruit for this apple. The subject of this application is a newly discovered sport of 'Jonnee' (U.S. Plant Pat. No. 2,934).

SUMMARY OF THE INVENTION

This new and distinct variety of Jonathan apple tree was discovered by me in 1985 as a limb mutation occurring on a Jonnee, (Robison Cultivar, U.S. Plant Pat. No. 2,934) tree in an orchard planted in 1970 on my farm near Bowling Green, Ky. The limb was located about 6 ft. off of the ground and growing upright in the parent tree. I first noticed it because the fruit started coloring about 30 days ahead of all other Jonnee, (Robison Cultivar) fruit in the orchard.

Observations during the next two seasons confirmed the early coloring and also that the fruit colored with a solid, bright red blush with no striping as opposed to the Jonnee, (Robison Cultivar, U.S. Plant Pat. No. 2,934) which colors with a distinct stripe and further that it matured 7 days earlier than its parent. The mature fruit finishes to a 100% solid, intense ruby red color with a smoother skin and less scarf skin and stem end russet that its parent. The internal flesh color is more yellow than the parent and has a more pleasing Jonathan taste.

In August of 1988, buds were taken from the original limb and trees for further testing and were asexually produced into 200 trees on my behalf by "The Nursery Corporation, Inc." (formerly Hilltop Orchards and Nurseries, Inc.), Hartford, Mich. 190 of these trees on MM 111 rootstock were all returned to me and used in testing and evaluation programs as follows using close friends in the Indiana, Illinois and Michigan area: 10 trees to Mr. Paul Anderson, Mooresville, Ind.; 40 trees to Mr. Bill Broom, Carlinville, Ill.; 10 trees to Mr. Bob Englebrect, Evansville, Ind., and 70 trees to Mr. Rex Anderson, New Castle, Ind. I planted the remaining 60 trees at my farm near Bowling Green, Ky. Additionally, 10 trees were produced on M26 rootstock. These were planted in a variety valuation at the Arden Winkle farm near Hartford, Mich.

All of these test trees have now fruited for 5 years and the test cooperator's reports confirm that the characteristics described above for the original limb are transmitted through to the next generation without change.

In summary, it has been confirmed that the new Jonathan variety, Jackson Cultivar, differs from its parent and other Jonathan varieties:

A. It starts coloring 30 days earlier that its parent; Robison (U.S. Plant Pat. No. 2,930), and Snyder (U.S. Plant Pat. No. 2,650); 50 days before the unpatented variety, Blackjon; 27 days before Uecker (U.S. Plant Pat. No. 85); 25 days before Carnefix (U.S. Plant Pat. No. 5,086); 20 days before Thome (U.S. Plant Pat. No. 8,701); and 19 days before Higred (U.S. Plant Pat. No. 6,406) as shown by the following graphic.

Relative dates of first color of Jonathan Cultivars

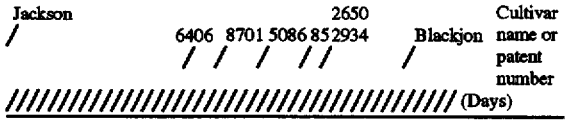

B. The fruit on the new variety matures 7 days earlier that the parent; Robison (U.S. Plant Pat. No. 2,934), Blackjon (unpatented), Snyder (U.S. Plant Pat. No. 2,650), and Uecker (U.S. Plant Pat. No. 85); and 3 days after Carnefix, (U.S. Plant Pat. No. 5,086), and Thome, (U.S. Plant Pat. No. 8701) as shown by the following graphic.

Relative maturity dates of Jonathan Cultivars

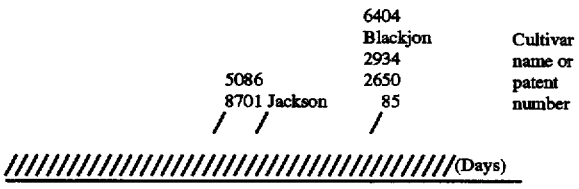

C. The color is a solid, bright red blush with no striping. It finishes to a 100% solid, intense ruby red blush with no stripe. Fan 1, Red Group 46 A to 45C. As opposed to Snyder, Thome, Higgins, Robison, Carnefix, and Blackjon which all exhibit striping characteristics.

D. The fruit finish is smoother with less scarf skin and stem end russet than the parent.

E. The internal flesh is more creamy yellow than the parent with the very pleasant taste of the original Jonathan variety.

BRIEF DESCRIPTION OF THE FIGURE OF THE DRAWING

The attached drawing depicts typical specimens of fruit of the discovery of this disclosure, 'Jackson' on the left, and from the parent variety 'Jonnee' on the right. Fruit from both trees was harvested on Aug. 26, 1993. On the left half of the photograph is a grouping showing specimens of the new tree 'Jackson'. On the left column of the grouping, specimens are shown in side view (top), of the blossom end (middle) and of the stem end (bottom); and, on the right, a specimen bisected to show seed carpels, core lines and flesh characteristics. On the right at the bottom is a further specimen depicted in side view. On the right side of the photograph is a grouping showing specimens of the parent tree 'Jonnee'. On the left of this grouping are shown a column with a specimen depicted in side view (top), of the blossom end (middle) and the stem end (bottom); and, on the right a specimen bisected to show seed carpels, core lines and flesh characteristics. On the right at the bottom is a further specimen depicted in side view. The solid red blush of 'Jackson' can be seen to differ from the striped to mottled skin color patterns of the parent 'Jonnee'.

DETAILED BOTANICAL DESCRIPTION OF THE TREE

A detailed description of my Jackson Cultivar Jonathan Variety follows using The Royal Horticultural Society of London Colour Chart for color identification except where general color terms are sufficient.

Parentage: A limb mutation of Jonnee,(Robison Cultivar, U.S. Plant Pat. No. 2,934). Locality of the original discovery and observations is Jackson Orchards, Slim Island Road, Bowling Green, Ky.

Tree:

*Size.*—Medium.
*Vigor.*—Vigorous.
*Density.*—Medium.
*Form.*—Upright, spreading.
*Production.*—Very productive.
*Bearing.*—Annual.
*Disease resistance.*—More resistant to stem end russet and scarfskin than parent.
*Ploidy.*—Probably diploid (2n=2x).

Trunk:

*Size.*—Medium stocky.
*Surface.*—Medium shaggy.
*Lenticils.*—Medium.
*Color.*—Fan 4, Grey Group 201D.

Branches:

*Size.*—Medium thick.
*Surface.*—Medium smooth.
*Form.*—Profuse branching.
*Buds.*—Alternate.
*Lenticils.*—Small, few, round to elongated.
*Color.*—1 year old branch: Fan 4, Black Group 202D. 2 year old branch: Fan 4, Grey Group 201A. 3 year old branch: Fan 4 Grey Group 201C.
*Leaves.*—*Size.*—Length — 73 mm, width — 39 mm.
*Form.*—Ovate to oval.
*Base.*—Rounded to slightly acute.
*Apex.*—Acute to slightly acuminate.
*Petiole.*—26 mm, color Fan 2, Red-Purple Group 61B.
*Margin.*—Simple serrate.
*Stipules.*—Prominent at base of petiole on most leaves.
*Venation.*—Pinnate 8–10 veins, mainly alternate.
*Pubescence*—None on adaxial surface, fine pubescence on abaxial surface.
*Color.*—Upper surface — Fan 3 Yellow-Green Group 146B. Lower surface — Fan 3, Yellow-Green Group 147B.

Flowers:

*Blooming period.*—April 8 to 14 in Bowling Green, Ky.
*Size.*—1.5 to 2.3 cm.
*Pollen.*—Profuse.
*Color.*—Fan 1, Red Group 56C at budding, fading to white at full open.

Fruit:

*Maturity when described.*—Firm ripe.
*Date of first picking.*—August 15, in Bowling Green, Ky.
*Date of last picking.*—August 30, in Bowling Green, Ky.
*Size.*—Axial diameter 2¼ to 2¾", transverse diameter 2½ to 3".
*Form.*—Uniform, symmetrical, regular, oblate truncate at base and apex.
*Cavity.*—Symmetrical, acute, depth ½" to ⅝", breadth ½".
*Basin.*—Symmetrical, abrupt at base, narrow, 5 crowed.
*Calyx.*—Closed, segments persistent, from acute to acuminate, erect, connivent. Outer and inner surfaces pubescent.

*Stem.*—Clubbed, medium stout, length 7/16" to ¾", curved, light pubescence.

*Bracts.*—Present, usually 2.

*Bloom.*—Medium.

Skin:

*Thickness.*—Medium.

*Texture.*—Very smooth, glossy with medium cuticle wax.

*Tendency to crack.*—None.

*Lenticels.*—Inconspicuous, small, few in number.

*Color.*—90 to 100% Fan 1 Red Group 46A to Fan 1 Red Group 45C, Ground color, Fan 1, Yellow Orange Group 23C.

Flesh:

*Texture.*—Crisp.

*Aroma.*—Strong, distinctive.

*Color.*—Fan 1, Yellow Group 4C.

*Flavor.*—Sub-acid with flavor of the original Jonathan.

*Eating quality.*—Best.

Core:

*Bundle area.*—Medium to ovate, cordate, symmetrical at base.

*Bundle.*—Inconspicuous, green, alternate above stamens.

*Capillary area.*—Distinct medium size.

*Calyx tube.*—Pubescent, narrow cone shaped, stem of funnel short.

*Depth of tube to shoulder.*—½".

*Styles.*—Distinct, pubescent.

*Stamens.*—One distinct whorl, medium.

*Axillary cavity.*—Wanting.

*Seed cells.*—Abaxile, walls thin, tough, length ⅔", breadth 3/16", longitudinal section-Broadly ovate.

*Seeds.*—5 to 8 perfect, length 7 to 10 mm, width 5 mm.

*Form.*—Acute.

*Color.*—Fan 4, Grayed Orange Group, 165A.

Use: Market desert.

Shipping quality: Excellent.

Keeping quality: Excellent, 3 to 4 months in common storage, 6 months or more in controlled atmosphere storage.

Disease resistance: Same as parent with better resistance to scarfskin and stem end russet.

We claim:

1. A new and distinct variety of apple tree, substantially as herein shown and described.

* * * * *

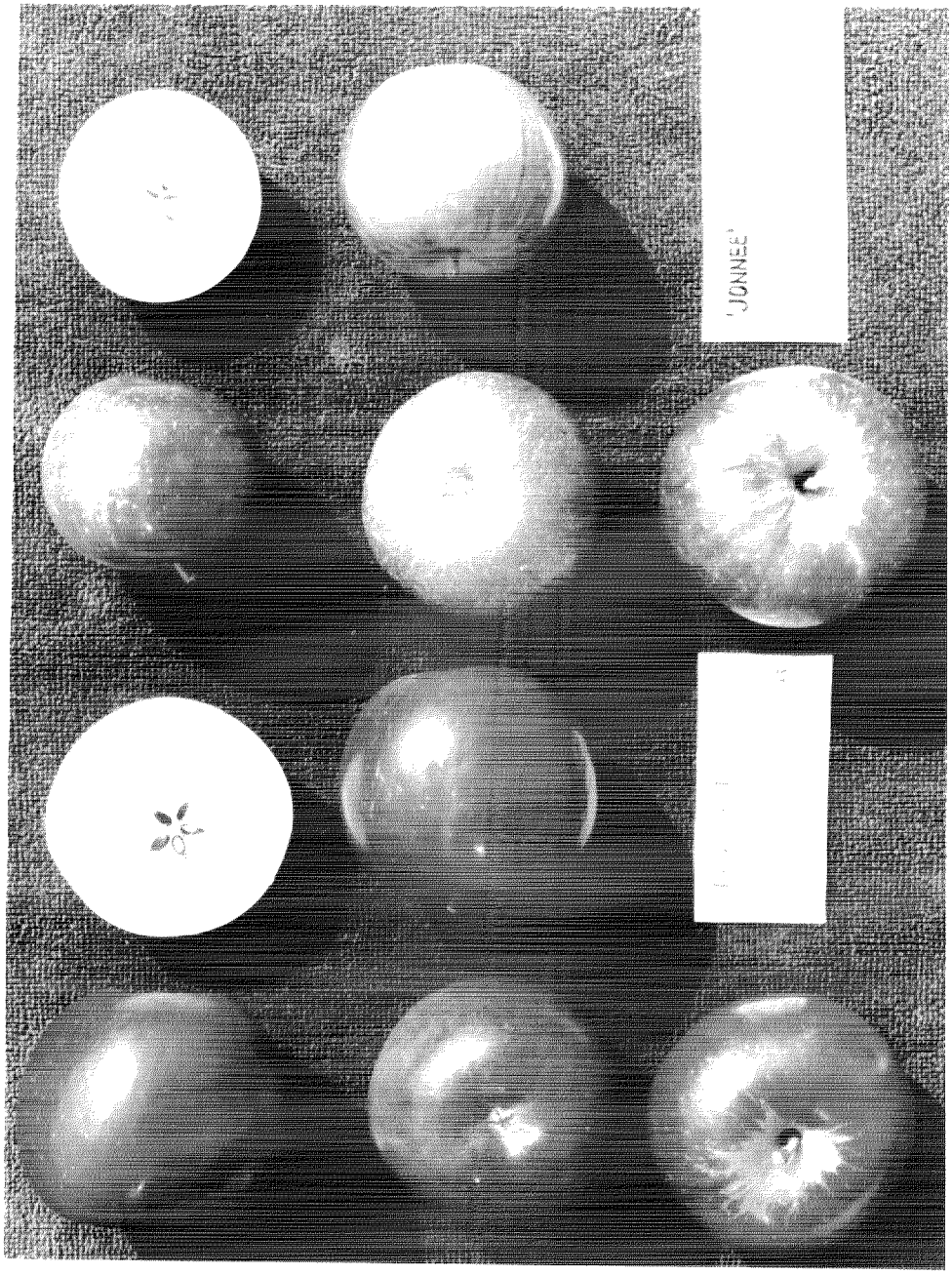
'JONNEE'